United States Patent [19]
Dotolo et al.

[11] Patent Number: 5,474,712
[45] Date of Patent: Dec. 12, 1995

[54] LIVESTOCK CONDITIONING SHAMPOO

[75] Inventors: John Dotolo; Vincent A. Dotolo, both of Clearwater, Fla.

[73] Assignee: Citra Science, Ltd., Largo, Fla.

[21] Appl. No.: 370,806

[22] Filed: Jan. 10, 1995

[51] Int. Cl.⁶ .................................................. C11D 1/14
[52] U.S. Cl. ............... 252/550; 252/174.15; 252/174.21; 252/174.27; 252/DIG. 13; 424/70.16; 424/70.12; 424/70.24; 424/70.11; 514/552; 514/549; 514/106; 514/517
[58] Field of Search ........................ 424/70.11, 70.12, 424/70.16, 70.24; 252/549, 106, 550, 174.11, DIG. 14, DIG. 5, DIG. 13; 514/582, 549, 106, 881

[56] References Cited

U.S. PATENT DOCUMENTS

| | | | |
|---|---|---|---|
| 5,296,156 | 3/1994 | MacGilp et al. | 252/108 |
| 5,378,731 | 1/1995 | Andrews et al. | 514/552 |
| 5,380,756 | 1/1995 | Andrews et al. | 514/552 |

*Primary Examiner*—Paul Lieberman
*Assistant Examiner*—Necholus Ogden
*Attorney, Agent, or Firm*—Donald R. Fraser

[57] ABSTRACT

A livestock conditioning shampoo consists of sodium lauryl sulfate, polyoxyethylene (20) sorbitan monolaurate, d-limonene, polyacrylic acid, acrylic copolymer emulsifier, butylated hydroxytoluene, triethanolamine, polyalkyleneoxide-modified polydimethylsiloxane, disodium EDTA, and water.

1 Claim, No Drawings

LIVESTOCK CONDITIONING SHAMPOO

FIELD OF THE INVENTION

This invention relates generally to a conditioning shampoo for the coats of livestock, and more particularly, to a formulation containing, inter alia, d-limonene which conditions the coats of animals yet is biodegradable.

BACKGROUND OF THE INVENTION

Many shampoo products are commercially available for cleaning and conditioning the coats of animals, e.g. horses. Often these products are harsh to the animal's skin and are additionally environmentally unfriendly.

It would be desirable to formulate a shampoo for livestock which cleans, deodorizes, and conditions the coats of said animals, assists in repelling flies and other insects, and is biodegradable.

SUMMARY OF THE INVENTION

Accordant with the present invention, a biodegradable livestock coat shampoo has surprisingly been discovered. The shampoo formulation consists of: sodium lauryl sulfate; polyoxyethylene (20) sorbitan monolaurate; d-limonene; polyacrylic acid; acrylic copolymer emulsifier; butylated hydroxytoluene; triethanolamine; polyalkyleneoxide-modified polydimethylsiloxane; disodium EDTA; and water.

The shampoo formulation of the present invention is particularly useful for cleaning and conditioning the coats of horses.

Further objects and advantages of this invention will be apparent from the following description and appended claims

DETAILED DESCRIPTION OF THE PREFERRED EMBODIMENTS

The shampoo formulation according to the present invention consists of a precise combination of sodium lauryl sulfate, polyoxyethylene (20) sorbitan monolaurate, d-limonene, polyacrylic acid; acrylic copolymer emulsifier; butylated hydroxytoluene; triethanolamine; polyalkyleneoxide-modified polydimethylsiloxane; disodium EDTA; and water.

Sodium lauryl sulfate acts as a wetting agent and thickener in the present formulation. The sodium lauryl sulfate may be present at a concentration from about 12 to about 38 weight percent. Preferably, the concentration is about 20 weight percent.

Polyoxyethylene (20) sorbitan monolaurate is included in the inventive shampoo as a surfactant and dispersing agent. The polyoxyethylene (2) sorbitan monolaurate may be present at a concentration from about 0.03 to about 2 weight percent. Preferably, the concentration is about 1 weight percent.

D-limonene is a terpene which occurs naturally in all living plants. It is a monocyclic unsaturated terpene which is generally a by-product of the citrus industry, derived from the distilled rind oils of oranges, grapefruits, lemons, and the like. A discussion of d-limonene and its derivation from numerous sources is set forth is Kesterson, J. W., "Florida Citrus Oil," Institute of Food and Agricultural Science, University of Florida, December, 1971. D-limonene is commercially available from Florida Chemical Company and from SMC Glidco Organics. D-limonene may be present in the shampoo formulation at a concentration from about 3 to 14 weight percent. Preferably, the concentration is about 8 weight percent.

Polyacrylic acid is added to the present formulation as a thickener. The polyacrylic acid may be present at a concentration from about 0.05 to about 1.2 weight percent. Preferably, the concentration is about 0.4 weight percent. A preferred polyacrylic acid is available from the BFGoodrich Company of Cleveland, Ohio under the product designation "CARBOPOL 980".

The inventive shampoo includes an acrylic copolymer emulsifier for producing a stable mixture of the ingredients. A preferred acrylic copolymer emulsifier is available from the BFGoodrich Company of Cleveland, Ohio under the product designation "PERMULEN TR-1". The acrylic copolymer emulsifier may be present at a concentration from about 0.03 to about 1 weight percent. Preferably, the concentration is about 0.5 weight percent.

Butylated hydroxytoluene is contained in the inventive formulation as an antioxidant. The butylated hydroxytoluene may be present at a concentration from about 0.02 to about 0.8 weight percent. Preferably, the concentration is about 0.1 weight percent.

Triethanolamine is present in the inventive shampoo as a humectant and softening agent, which is important for conditioning the coats of the animals to which the shampoo is applied. The triethanolamine may be present at a concentration from about 0.75 to about 2.3 weight percent. Preferably, the concentration is about 1.3 weight percent.

A polyalkyleneoxide-modified polydimethylsiloxane is included in the inventive shampoo, as an antifoaming agent. A preferred polyalkyleneoxide-modified polydimethylsiloxane is available from Amerchol Corporation of Edison, N.J. under the product designation "AMERSIL DMC-357". The polyalkyleneoxide-modified polydimethylsiloxane may be present at a concentration from about 0.2 to about 0.9 weight percent. Preferably, the concentration is about 0.5 weight percent.

Disodium EDTA is included in the present formulation as a chelating agent. The disodium EDTA may be present a concentration from about 0.05 to about 0.8 weight percent. Preferably, the concentration is about 0.1 weight percent.

Water constitutes the balance of the shampoo formulation of the present invention.

The ingredients may be combined and mixed in conventional mixing apparatus, to prepare the shampoo according to the present invention. The resultant formulation may then be applied directly to the coats of animals to clean, deodorize, and condition same. The inventive formulation is particularly useful for cleaning and conditioning the coats of horses. Additionally, the formulation assists in repelling flies and insects from the coats of the livestock upon which it is used.

In accordance with the provisions of the patent statutes, the present invention has been described in what is considered to represent its preferred embodiment. However, it should be understood that the invention can be practiced otherwise than as specifically illustrated and described without departing from its spirit or scope.

EXAMPLE

The following ingredients are mixed together in the approximate weight percentages indicated, to form a conditioning shampoo. The shampoo is then applied to the coats of animals in a conventional manner, to clean and condition same.

TABLE 1

SHAMPOO FORMULATION

| Ingredient | Weight Percentage |
|---|---|
| sodium lauryl sulfate | 20 |
| polyoxyethylene (20) sorbitan monolaurate | 1 |
| d-limonene (1) | 8 |
| polyacrylic acid (2) | 0.4 |
| acrylic copolymer emulsifier (3) | 0.5 |
| butylated hydroxytoluene | 0.1 |
| triethanolamine | 1.3 |
| polyalkyleneoxide-modified polydimethylsiloxane (4) | 0.5 |
| disodium EDTA | 0.1 |
| water | 68.1 |

(1) GLIDSAFE, from SMC Glidco Organics.
(2) CARBOPOL 980, from the BFGoodrich Company.
(3) PERMULEN TR-1, from the BFGoodrich Company.
(4) AMERSIL DMC-357, from Amerchol Corporation.

This Example may be repeated with similar success by substituting the generically or specifically described ingredients and/or concentrations recited herein for those used in the preceding Example.

From the foregoing description, one ordinarily skilled in the art can easily ascertain the essential characteristics of this invention and, without departing from its spirit or scope, can make various changes and modifications in the invention to adapt it to various usages and conditions.

What is claimed is:

1. A conditioning shampoo, consisting of:

from about 12 to about 38 weight percent sodium lauryl sulfate;

from about 0.03 to about 2 weight percent polyoxyethylene (20) sorbitan monolaurate;

from about 3 to abut 14 weight percent d-limonene;

from about 0.05 to about 1.2 weight percent polyacrylic acid;

from about 0.03 to about 1 weight percent acrylic copolymer emulsifier;

from about 0.02 to about 0.8 weight percent butylated hydroxytoluene;

from about 0.75 to about 2.3 weight percent triethanolamine;

from about 0.2 to about 0.9 weight percent polyalkyleneoxide-modified polydimethylsiloxane;

from about 0.05 to about 0.8 weight percent disodium EDTA; and the balance, water.

* * * * *